United States Patent [19]
Snyder, Jr. et al.

[11] Patent Number: 5,674,513
[45] Date of Patent: Oct. 7, 1997

[54] ANTI-BACTERIAL/ANTI-VIRAL COATINGS, COATING PROCESS AND PARAMETERS THEREOF

[75] Inventors: Donald E. Snyder, Jr., Brockport; Joni L. Best, Rochester; Donald A. Gorall, Webster, all of N.Y.

[73] Assignee: Viro-Kote, Inc., Dallas, Tex.

[21] Appl. No.: 603,783

[22] Filed: Feb. 20, 1996

[51] Int. Cl.$^6$ ........................................ A01N 25/34
[52] U.S. Cl. .................. 424/404; 424/409; 424/414; 424/447
[58] Field of Search ........................... 424/404, 409, 424/414, 447; 423/236, 245, 289

[56] References Cited

U.S. PATENT DOCUMENTS

| | | | |
|---|---|---|---|
| 4,401,712 | 8/1983 | Morrison | 428/289 |
| 4,411,928 | 10/1983 | Baldwin | 427/2 |
| 4,575,891 | 3/1986 | Valente | 15/104.93 |
| 5,006,339 | 4/1991 | Bargery et al. | 424/404 |
| 5,019,096 | 5/1991 | Fox, Jr. et al. | 623/1 |
| 5,087,450 | 2/1992 | Lister | 2/161 R |
| 5,091,102 | 2/1992 | Sheridan | 252/91 |
| 5,130,159 | 7/1992 | Shlenker et al. | 427/2 |
| 5,165,953 | 11/1992 | Shlenker et al. | 424/402 |
| 5,181,276 | 1/1993 | Kersten et al. | 424/78.36 |
| 5,236,703 | 8/1993 | Usala | 424/78.36 |
| 5,380,523 | 1/1995 | Digenis et al. | 424/78.25 |
| 5,492,692 | 2/1996 | Digenis et al. | 424/78.25 |

OTHER PUBLICATIONS

Montefiori et al., "Evaluation of Antiviral Drugs and Neutralizing Antibodies to Human Immunodeficiency Virus by a Rapid and Sensitive Microtiter Infection Assay," *J. Clin. Microbiology*, 1988, vol. 26:231-235.

*Primary Examiner*—Thurman K. Page
*Assistant Examiner*—Kathryne E. Shelborne
*Attorney, Agent, or Firm*—Fay, Sharpe, Beall, Fagan, Minnich & McKee

[57] ABSTRACT

The invention relates to a method of imparting anti-pathogenic properties to a substrate material comprising: (a) preparing a coating composition containing an anti-pathogenic agent consisting essentially of PVP-I and N-9 in a ratio of from about 100:0 to about 0:100 of PVP-I to N-9, the coating composition further containing a pre-mix solution with which the anti-pathogenic agent is intimately mixed in a ratio of from about 6:4 to about 8:2 of agent to pre-mix on a dry basis, and having a percent solids content of from about 5% to about 35% solids; (b) feeding the anti-pathogenic coating composition into a coating machine; (c) loading substrate onto the coating machine; (d) operating the coating machine such that the coating composition comes into intimate contact with at least one surface of the substrate; and (e) drying the coated substrate material. The invention further relates to the preparation of coating composition and to the composition itself.

24 Claims, No Drawings

ANTI-BACTERIAL/ANTI-VIRAL COATINGS, COATING PROCESS AND PARAMETERS THEREOF

BACKGROUND OF THE INVENTION

The invention relates to a method for coating a substrate with an anti-pathogenic agent to render the substrate suitable for use as a barrier against pathogens. Specifically, the invention provides a method for coating a range of substrates with an anti-pathogenic agent such that in the dry state the substrate acts as a barrier to block the progress of pathogens and in the wet state the substrate coating is activated to release the anti-pathogenic agent and eliminate pathogens upon contact thereof with the agent. The invention further relates to various methods of coating substrates and to the products produced according to the methods.

It is well known in the related technology field to incorporate an anti-bacterial agent into a material or fabric intended for use in medical applications to guard against the transfer of contagious and potentially lethal pathogens. The incorporation of such agents has been accomplished by coating the outer surface of the material, by interply coating of multi-ply fabric or material, or by chemically incorporating the coating agent into the material at the time of production.

Further, the use of various agents has been reported. For example, agents have been successfully incorporated into medical-type materials, whether paper or polymeric in nature, to guard against the spread of infection. Among those agents which have been coated onto or incorporated in paper-based substrates are bisoxirane compounded with phenolic active agents (U.S. Pat. No. 4,855,139); silicone quaternary amine agents (U.S. Pat. No. 4,736,467); 2-amino-4-oxo-tricyclicypyrimidine antiviral agents (U.S. Pat. No. 4,625,026); monocarboxylic acid antimicrobial agents (U.S. Pat. No. 4,430,381); and the use of polyvinylpyrrolidone-iodine complex as a broad spectrum anti-microbial agent (U.S. Pat. No. 5,069,907). Similar agents have been used in preparing materials comprising polymeric compounds that exhibit anti-vital characteristics. For example, nonoxynol-9 (U.S. Pat. No. 5,130,159); organosilicone quaternary ammonium compounds (U.S. Pat. No. 5,126,138); and biguanide(chlorhexidine) (U.S. Pat. No. 4,999,210). It has further been shown to use nonoxynol-9, a known spermicide, in conjunction with PVP-I complex, a known bactericide, in the high energy coprecipitate form to protect against the spread of viral and bacterial infection, including the HIV virus (U.S. Pat. No. 5,380,523). Many of the foregoing, however, represent products or compounds which if used in the manner contemplated herein and fully disclosed hereinafter would prove irritating to the skin or difficult to commercially produce. Moreover, the prior attempt at using the high energy coprecipitate of PVP-I/N-9, while it does achieve the desired anti-viral result, is of limited commercial value due to complications in manufacture and use of the product disclosed.

It is, therefore, an object of the subject invention to provide an anti-pathogenic coating to a medical-type substrate in a commercially viable manner.

BRIEF SUMMARY OF THE INVENTION

The invention generally relates to a method of imparting anti-pathogenic properties to a substrate material by coating the substrate with a coating composition containing an anti-pathogenic agent consisting essentially of PVP-I and N-9 in a ratio of from about 100:0 to about 0:100 of PVP-I to N-9, the coating composition further containing a pre-mix solution with which the anti-pathogenic agent is intimately mixed in a ratio of from about 6:4 to about 8:2 of agent to pre-mix on a dry basis, and having a percent solids content of from about 5% to about 35% solids. The invention further relates to the preparation of the coating composition and to the composition itself.

DETAILED DESCRIPTION

Statement of Invention

The subject invention relates to a process for producing substrates coated with a formulation containing a novel anti-pathogenic component. Upon contact of the coated substrate with a pathogen-containing material, the anti-pathogenic component is released to eliminate any pathologic affect of the pathogen. The invention further relates to the preparation of the anti-pathogenic-containing formulation, to the coating process, and to products or articles prepared from the coated substrates and their use.

As used herein, the term "coated substrate" refers to any substrate which ultimately, in finished form, contains the anti-pathogenic component, whether the component is coated on the surface of the substrate, is imbedded in the substrate during substrate production, or is included in the finished substrate in another manner, as described hereinafter.

Also, the term "pathogen" and "pathogenic properties" in its various forms is used herein to mean and include such terms as viral, bacterial and HIV. Therefore, reference to an "anti-pathogen" or "anti-pathogenic property/activity" includes reference to anti-vital, anti-bacterial and/or anti-HIV compositions and their anti-vital, anti-bacterial and/or anti-HIV activity. The term is used to refer to the use of the subject formulation, coated on an appropriate substrate, to neutralize or eliminate the undesirable affects of a pathogen by protecting against contact with the pathogen and further, upon contact with bodily fluids and/or skin, by eliminating the pathogenic activity.

BASIC DESIGN

Coating Techniques

For high speed web coating of solvent formulations, common coating techniques include reverse roll, rod, and gravure coating methods. Roll coating methods further include kiss coating, single roll coating, and double roll coating, among others. Reverse roll, rod, and gravure coating techniques are preferred herein because they offer the ability to put down uniform coatings at high speeds, as well as the ability to use formulations with medium to high solids content, thus minimizing wasted solvent which is volatilized in the drying process.

The reverse roll coating method is commonly used to apply heavy to light weights of coatings, but has limited capability for very fight weight coating application, below about 1lb/3,000 ft². In this coating method the web, or substrate, travels at surface speed around a first, rubber roll while in contact with a second steel applicator roll which is rotating at high speed in the opposite direction at the point of contact. A third metering roll contacts the applicator roll. The coating formulation is transferred from the applicator roll onto the web. Viscosity, percent solids, and specific gravity of the coating formulation affect coating quality and coat weight, as well as mechanical parameters, such as the pressure setting between the applicator rob and the rubber roll, differential speed of the rollers with respect to each other, and the gap between the applicator and metering robs.

Rod coating involves passing the substrate web over an applicator roll that turns in the liquid coating formulation, transferring an excess of coating to the bottom side of the web. The excess is removed by means of a wire of specific gauge which is wound around a rod positioned behind the applicator roll. The rod is generally ⅛ inch to ½ inch in diameter, and the wire gauge generally runs from 3 gauge up to 32 gauge or higher. The choice of wire gauge determines the resulting coat weight. Of course, parameters of the coating formulation, i.e., such as viscosity and total solids, and other mechanical parameters also affect coating weight.

Gravure coating, as used herein, operates on the same principles that the gravure printing method operates on, except that in this instance the goal is to achieve 100% coverage of the substrate. Because this method involves the deposition of coating material in a pattern dictated by the cell pattern design and depth on the gravure cylinder, the coating formulation must be sufficiently fluid to flow and transfer to the substrate prior to drying in order to result in a continuous coating. This method is generally more suitable for the deposition of lower coating weights, as compared to reverse roll and rod coating. The mount of coating used is more accurately metered by this method, making it a viable option.

One limitation of the foregoing coating techniques is that they require the use of substantially non-porous substrates. If the substrate is excessively porous, it becomes difficult to control coat weight and to properly track the web through the coating machine, i.e., the coating may offset onto the machine rolls.

For paper and film substrates, this does not generally pose a problem. Most papers and films have sufficient coating hold-out or, in other words, are sufficiently non-porous. Occasionally, a paper substrate may be excessively porous and require an alternate coating technique to be used.

For the reasons just stated, non-woven substrates, the majority of which tend to be porous, do not lend themselves to conventional solvent coating techniques such as reverse roll, rod, or gravure. In these cases, several alternate approaches to coating the substrate may be taken, for example: fabric treatment which enables the coating to be applied; the use of non-woven fabric laminated to a film or other impervious substrate, which is a viable solution given the current increase in the use of non-woven laminates in medical markets for a variety of reasons; and the use of alternate coating techniques, which may require formulation modification.

Suitable alternate coating techniques for use with the subject invention include spray and dip coating techniques.

Spray coating is highly suited to use for more porous substrates because it affords greater control over penetration of the coating into the substrate. With spray coating the coating formulation is essentially atomized into a free mist so that it can be applied to the porous substrate without excess penetration to the opposite side of the substrate, assuming heavy coat weights are not applied. However, the spray coating could also be applied to both sides of the web, if desirable. In order to atomize the coating formulation, it should be tied. Proper atomization of the coating is important to the even and uniform application of the coating, as are the amount and pressure of air flow. Disadvantages of the spray coating technique are that atomization generally requires a formulation having lower solids, therefore wasted solvent and overspraying may be problems. Further, it can sometimes be difficult to control coat weight uniformity when using the spray coating technique.

Dip coating is another viable alternative coating method. Dip coating is probably the simplest form of coating in terms of equipment, however uniformity of coating requires that great care be taken to control the rate of withdrawal of the substrate from the coating, solvent evaporation, drainage, etc. In this technique, the substrate is passed from a lead-in roll to an immersion roll placed in or over a coating pan. The immersion roll is positioned high or low depending on the desire to coat only one or both sides of the paper. This method, like spray coating, requires low solids content of the coating formulation and is significantly affected by the porosity of the substrate, as well as by environmental and mechanical parameters. In dip coating, the entire non-woven substrate is immersed in the coating and the substrate is impregnated. Because a lower solids formulation is typically required, environmental concerns due mostly to solvent evaporation must be addressed.

For spray and dip coating, the standard formulation is typically diluted to generally 5–20% solids, preferably 10% solids, as compared to a 25%–35% solids range usable with roll coating methods and techniques. In addition, the coating formulation can be modified in other manners regarding component content levels to achieve coatable solutions for a given technique.

Substrates Suitable for Use in Conjunction With the Anti-Pathogenic Formulation

Suitable substrates for use in conjunction with the anti-pathogenic formulation described hereinafter include substrates, including but not limited to, paper, paper laminates, non-woven materials, non-woven laminates, and other similar substrates. The invention is primarily concerned with substrates targeted for use in medical-type applications, such as surgical gowns and drapes, examining table paper, hospital bed pads, hospital bed inserts and sheeting, surgical masks and other hospital or medical-type applications which will be readily apparent to the skilled artisan after reading and understanding the technology disclosed herein. The term "medical" as used herein further includes the use of the described and similar items in dental and other medically related environments, i.e. tray liners and instrument wraps, masks, dental patient bibs, etc.

While the primary use of the invention is in the medical-type environment, it is also envisioned that the coated substrates described will find application in personal hygiene type uses, such as toilet seat covers. This type of item includes not only publicly provided items, but also personal items which can be carded by an individual for private use.

Given the variation in the useful environments for the intended application of these coated substrates, there is a wide variety of potential substrate materials.

I. Paper Substrates

One potential substrate is paper, which once coated may be used, for instance, as examining table roll or cover where there is a high risk of exposure to bacteria and other viral pathogens. Other uses for coated paper products include troy liner paper for surgical or medical instrument trays, wrapping for sterilized surgical or medical instruments, medical packaging paper, and other uses.

For the foregoing and other similar applications, appropriate paper substrates include medium weight papers which are not too flimsy, and therefore do not easily tear or shred, but which are also not too heavy. The paper must be able to withstand winding tensions on a web coating machine or apparatus without suffering performance degradation. Further, papers suitable for this application should exhibit good hold out, which is closely related to the porosity of the substrate and is exhibited by the capability of the paper to maintain the coating without penetration or bleed through. Other characteristics which will affect the suitability of a paper substrate for use in this invention include the tensile strength of the paper, the stiffness of the paper, drapeability, alcohol and water repellency, bursting strength, air permeability, flammability, and abrasion and tear resistance. It is intended that these paper substrates, once coated, act as a barrier to bacteria and viruses in the dry state, and become activated, releasing the anti-pathogenic component, to eliminate bacteria and viruses when wet.

Specific examples of suitable paper substrates include standard paper substrates made from wood pulp and processed with cellulosic fibers. For example, suitable grade paper for the intended processing and uses may be selected from papers ranging between 17.5 lb. to 20 lb. per 3000 ft$^2$, available currently from James River Corporation under the Flexpat tradename, specifically BL FLEXPAC 20 TM LG, 17.5# to 20.0#, and even a 13 lb. per 3000 ft$^2$ grade paper available commercially from Coastal Paper Company by the designation BL MG PR HWS. The preferred grade of paper, then, is probably in a range between about 10 lb. per 3000 ft$^2$ to about 30 lb. per 3000 ft$^2$, with the selection within this range being dependent upon the intended use, i.e., the lighter weights may be suitable examining table paper while the heavier weights would be better suited to paper gowns. This range, however, may be extended beyond the stated limits as long as the paper substrate can meet the criteria stated above for processing and use, mechanically as well as with respect to release of the anti-pathogenic agent.

Coated papers and synthetic papers may also be suitable for use herein. For example, acceptable coated papers may be a cellulose based paper coated with an acrylic coating, such as Kimberly Clark's currently available 2.5 lb. per 3000 ft$^2$ S-60857 product.

II. Paper/Film Laminates

Paper/film laminate substrates in which the paper substrate is generally laminated to a polymeric film are also suitable paper substrates. They find particular application to the uses specified above with respect to paper substrates, but are further suitable in other applications where durability and low porosity are important considerations. The film component of a paper/film laminate is usually a material such as polyethylene, polypropylene or polyurethane, which enhances the hold-out of the substrate preventing the coating from penetrating through the composite.

With respect to the foregoing paper and paper laminate substrates, it should also be understood that a further consideration in selecting a substrate is whether the product is intended to be disposable or non-disposable, and if disposable, the likely manner in which the product will be disposed. For instance, consideration may be given to whether the product will be discarded with other medically related disposable items, or discarded with other non-medically related items in normal disposal situations, or whether there is a possibility of disposal by flushing, as in the case of toilet seat covers.

For items which will be disposed of in medical and/or non-medical refuse situations, biodegradability is desirable. Flushable items must exhibit poor wet strength, and yet have good hold out. Suitable flushable paper substrates include those available from Coastal Paper, such as 13# BL MG PR HWS and 14.4# BL MG DUNECON SH, which are lightweight bleached coating base tissues. Non-flushable paper substrates include Coastal Papers' 10.5# BL MG HWS for which the wet strength is too high, and paper laminates from Jen-Coat identified as Jen-Coat 19# Semi Crepe/5# LDPE Matte laminate (low density polyethylene).

In all instances, the paper substrates described hereinabove, including paper laminates, should be selected according to the ability of the paper to retain the coating to a degree sufficient to ensure elimination of bacterial or viral contamination. The product functions as a barrier to the virus and bacteria when dry, and actively eliminates or kills the virus or bacteria on contact when wet. Coated paper substrates with these qualifies are suitable for use in a multitude of medically related and personal hygiene applications as described hereinabove.

III. Non-Woven and Non-Woven Laminate Substrates

Non-woven substrates include such substrates as spun bonded fabrics and two-phase fabrics. Spun bonded fabrics are those formed from continuous filaments that have been extruded, drawn, laid on a continuous belt in a three-dimensional arrangement, and immediately thermally bonded to form a "web" of material. The extruded filaments have a thickness on the order of about 20μ.

Another type of non-woven material available is a fabric called spunlaced fabric. This fabric is a three-dimensional structure resulting from the hydroentanglement of staple or base fibers without any chemical or thermal bonding, thus providing a material demonstrating excellent flexibility, softness and drape. The fabric may be composed of a single type of fiber, or may be a blend of fibers, with varying content ranges. For example, the fabric may be a rayon/polyester blend, a wood pulp/polyester blend or 100% polyester fiber. Fabric content is highly determinative of suitability for a specified purpose, i.e., durability, strength, absorbency and other properties are directly affected by fabric content.

SONTARA®, a DuPont product, is a spunlaced product available in a wide range of weights and in varying fiber contents. Of particular interest herein are those fabrics of a wood pulp/polyester blend, which adapt well to use in hospital gowns and drapes, and those of a rayon-polyester blend which perform well as absorbent wipes and sponges, and when pre-treated, as repellent barrier materials having high comfort qualities.

While non-woven substrates offer many advantages, they also represent special coating considerations. Often, non-woven substrates have been treated to enhance water and even alcohol repellency. Thus, many of these fabrics are attractive as operating room fabrics. These fabrics, however, are more likely than other substrates to experience coating absorption and penetration. To protect against these potential problems, which may occur with traditional web coating techniques, spray or dip coating methods have been found herein to provide suitable alternatives. When using these methods the subject formulation is modified, generally to achieve a thinner formula with lower solids content.

Non-woven laminates are those materials such as the non-woven substrates described above which have a laminate layer or a laminate backing to aid in solving potential absorption and penetration problems. In these fabrics, the non-woven material substrate is generally laminated to a film such as polyethylene, polypropylene or polyurethane. The film enhances the hold-out of the substrate, preventing the coating from penetrating through the non-woven composite.

Alternatively, the non-woven laminate may be a combination of non-woven fabric with a microporous film laminated thereto. This microporous film is generally a breathable film, which means that the film allows air to penetrate, but prevents the penetration of liquids. The moisture vapor transmission rate (MVTR) is a measure of the amount of moisture vapor that passes through a fabric. Fabrics with high MVTR, therefore, are cooler for the person wearing the garment than a lower MVTR fabric. Also, water vapor is smaller than droplets of blood and is, therefore, more readily passed through the micropores of the non-woven substrate. The practical result of the forgoing is that though moisture is transported through the fabric's micropores to keep the wearer of a high MVTR fabric gown comfortable, there is little danger of blood droplets, which may carry any number of pathogens, penetrating the gown or fabric and reaching the wearer. Specific examples of non-woven laminates include the following substrates marketed by Polybond, Inc.: Poly-Breathe I spunbonded polypropylene non-woven/ polyethylene microporous film; Poly-Breathe II spunbonded polypropylene/heavy duty microporous film; and Poly Breathe Soft spunbonded polyethylene/microporous film having excellent drapeability.

Usually, the micro-porous film side of the laminate is most easily coated with the formulation which is the subject hereof because of superior hold- out which better lends itself to traditional web coating techniques. However, the non-woven fabric side of the laminate may be coated by alternate coating techniques if it is desirable for functional purposes. Other suitable non-woven fabric laminations include Bertek's Mediffim 432, which is a laminate of polyurethane film direct extrusion laminated onto SONTARA 8001 polyester fabric. Further, the non-woven may be a wood pulp/ polyester blend such as SONTARA 8818 or 8801. The wood pulp/polyester blends are especially engineered as fabrics for medical applications due to their softness and high absorbency. The substrates also can be treated to repel liquids. The laminations cited above find particular applicability in medical garment and in wound care fabrics or products.

The foregoing substrates are exemplary only. Any number of other substrates will be known to the skilled artisan, and are intended to be covered by the teachings herein, as long as the substrate maintains its integrity through the coating process, accepts the coating formulation and supports it in a manner whereby the anti-vital, anti-bacterial activity of the coating is not adversely affected to a point where it is no longer suitable as an anti-pathogenic coating, and the coated substrate is suitable for adaptation or application to use in the medical or personal hygiene fields.

Coating Formulation

The subject coating formulation is an anti-vital, anti-bacterial, composition, having anti-HIV activity as well, which is intended for use in all aspects of medical applications, including dental applications, and in various personal hygiene applications. The composition contains as the active ingredient therein a combination of nonylphenoxypoly (ethylene oxy) ethanol, more commonly known as Nonoxynol 9 or N-9, and a Polyvinyl-pyrrolidone-Iodine complex, or PVO-I.

The Nonoxynol 9 component is a commercially available composition which is known to exhibit spermicidal activity. It can be purchased from Rhone Poulenc in the liquid form.

The PVP-I component is known to exhibit anti-microbial properties, including anti-HIV activity. It is available in the powder form from sources such as GAF and BASF. The PVP portion of the complex contributes unique hydrophilic properties. The iodine portion of the complex is effective as a bactericide in its $I_2$ or diatomic form.

The foregoing active ingredients, when combined and further mixed with various additives, exhibit superior anti-HIV and anti-vital/anti-bacterial activity, making the subject formulation highly suitable, and desirable, as a candidate for the coating of substrates which are used as a barrier against the propagation of viruses and various forms of bacteria which are highly infectious. Because these products are intended for use in situations where the product may come in direct contact with the users' skin, it is imperative that the effectivity level of the coating be closely monitored.

Specifically, it has now been discovered that in a solution containing the anti-vital components just described, intended for coating on the various substrates by general coating techniques as described herein, sufficient anti-viral activity is achieved along with optimal coating properties in a solution characterized by percent solids (non-volatiles) of 25.0% to 35.0%, and ideal viscosity, depending on the formulation used and the rheological characteristics thereof, of from about 50 to 600 cps. These properties are exhibited by the formulation described hereinafter.

The active ingredients may be combined in a ratio of PVP-I:N-9 of 100:0 to 0:100. A combination of the two anti-vim/components provides flexibility to change the ratio so that the formulation can be tailored to a specific application. When the intended purpose is use of a product against bacterial infection (e.g. in a toilet seat cover), it may be advantageous to use a greater percentage of PVP-I. Obviously, the exact combination of active ingredients is dependent on the end use of the product and the pathogens to be eliminated.

Generally, the subject composition contains Nonoxynol 9 and PVP-I in combination with various agents used as filler, lubricants, binder, suspending agent, surfactant and stabilizer. The Nonoxynol 9, or N-9, component has the following formula:

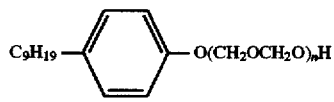

wherein n represents the number of ethylene oxide units. This polymer, available commercially from Rhone Poulenc under the tradename Igepal CO-630, contains at least 17 oligomers of varying ethylene oxide chain length. The molecule N-9 contains a hydrophobic moiety, the nonylphenol portion of the molecule, and a hydrophilic chain composed primarily of ethylene oxide units. The physical and chemical characteristics of the oligomers change as a function of chain length. For instance, in those oligomers where n=1–6, the oligomer is oil soluble, and these compounds exhibit greater dermal toxicity with respect to fibroblasts. Further, lower molecular weight oligomers, for instance, the n=9 oligomer, exhibit greater in-vitro spermicidal activity than those molecules where n=30 or higher.

The PVP-I complex represents polyvinylpyrrolidone, or providone USP, complexed with iodine which has been shown to exhibit anti-HIV activity in addition to general anti-microbial activity. The PVP portion of the complex is one of the most highly utilized polymers in medicine due to its safety for human use and its hydrophilic nature when complexed with iodine at a 10% w/v level. A 10% w/v PVP-I solution contains approximately 1% of available $I_2$, the $I_2$ content being about 9–12%. The complex efficiently delivers anti-microbial $I_2$ (free iodine) at a relatively non-toxic, non-irritating rate. The hydrophilic PVP polymer, therefore, acts as a means for delivering free iodine to solution from the complex which is important because the free iodine functions to eliminate vital or bacterial pathogens, including the HIV virus. Because commercially available PVP-I material is in a complexed form in which a true chemical bond apparently exists between the PVP and iodine constituents, it is provided in a detoxified form found to be non-irritating to human skin, thus eliminating these concerns with respect to the subject invention.

The coating composition further includes a hydrophilic polymeric binder which further functions as a dispersant or suspension agent. Suitable agents include modified cellulose materials, such as methylcellulose, hydroxyethylcellulose, hyaroxymethylethylcellulose and hydroxypropyl methylcellulose (HPMC). This agent is non-toxic and therefore safe for inclusion in coatings which will come in contact with human skin.

Talcum, or natural hydrous magnesium silicate, in foliated form, also known as talc, is included in the subject composition as a filler and lubricating agent. Substitutes for talc include titanium dioxide and calcium carbonate.

A surfactant is included in the coating composition to aid in control of the theology of the coating by reducing surface tension. One nonionic suffactant suitable for use herein is obtained by esterification of sorbitol with a fatty acid under conditions which cause the splitting out of water from the sorbital, leaving sorbitan. This suffactant is nontoxic and soluble in water, alcohol and ethyl acetate. The suffactant prepared is polyoxyethylene sorbitan monooleate. Tween 80 is a commercially available polyoxyethylene sorbitan monooleate marketed by Spectrum. Other suitable suffactants will be known to the skilled artisan.

Polyethylene glycol is added to the composition as an excipient. This component functions as a lubricant, plasticizer, binder and suspending agent. The polyethylene glycol is soluble in ethanol and water, has low toxicity and is a stable compound. One suitable polyethylene glycol product is Carbowax, available commercially from Union Carbide. An acceptable molecular weight range for the polyethylene glycol component is dependent upon the remaining formulation components, however, Carbowax 1450 grade (average molecular weight range 1300 to 1600) to Carbowax 8000 grade (average molecular weight range of 7000 to 9000) is generally suitable for the subject formulation. Further, it is preferred to use Sentry grade product produced to meet National Formulary (NF) and Food Chemical Codex (FCC) specifications for food, drag and cosmetic applications.

The following general formula is suitable for use in traditional web coating techniques, such as reverse roll, rod coating, gravure coating, etc.

| General Coating Formulation | | |
|---|---|---|
| Component | | Percent Composition |
| Active Ingredient Solution | | 30–80% |
| N-9 | 0–100% | |
| PVP-I | 0–100% | |
| Pre-mix Solution | | 20–70% |
| Polyethylene Glycol solution | 30–85% | |
| Hydroxypropyl methylcellulose | 2–20% | |
| Polyoxytheylene sorbitan compound | 2–10% | |
| Hydrous magnesium silicate | 5–15% | |
| Ethanol Solvent | 0–30% | |
| | | 100.0 |
| | | % solids 20% to 35% |

One embodiment of the invention relates to the preferred method for producing the above coating composition. The coating formulation prepared below (Formulation 2) has 71.5% Active Ingredient Solution and 28.5% Pre-mix Solution, with a % solids of 31.4% and a viscosity of between 90 and 130 cps.

Initially, a pre-mix solution is prepared comprising a polyethylene glycol (Carbowax) solution, talc, hydroxypropyl methylcellulose (I-IPMC), and polyoxyethylene sorbitan monooleate (Tween 80). The solution of Carbowax is prepared by adding Carbowax to an ethanol/water mixture in the following proportions:

| Carbowax Solution (IA) | |
|---|---|
| Component | Percent |
| Carbowax 8000 (Sentry Grade) | 20.0 |
| Distilled Water | 32.0 |
| Ethanol 190P | 48.0 |
| | 100.0 |
| | % solids (theoretical) 20% | where the Ethanol 190P is a solvent blend ethanol product, available commercially from Ashland Chemical, which contains 87% ethyl alcohol, 4% methyl alcohol, 2% methyl isobutyl ketone, and 3–7% water. Other suitable solvents include other ethanols, methanol, and mixtures of ethanol or methanol and water.

To the Carbowax solution is added Tween 80 and Ethanol 190P with stirring.

In a separate container, Dow Methocel E15LV hydroxypropyl methylcellulose powder and talc T1005 dry powder are combined. In this instance, Dow Methocel E15LV and T1005 respectively may be used, though other suitable commercial products will be known to the skilled artisan. Alternatively, these powder components could be added individually directly to the pre-mix solution, slowly and with high shear mixing. Combining the powders prior to addition to the premix results in easier and more efficient assimilation of the HPMC resin into the pro-mix.

Once the powders are fully mixed, the mixture is added slowly to the pro-mix solution, increasing the mixing speed as the mixture thickens. Stirring is continued for at least 30 minutes, until a homogenous mixture is obtained.

| Pre-Mix Solution (1B) | |
|---|---|
| Component | Percent |
| Carbowax Solution (IA) | 54.6 |
| HPMC | 5.4 |
| Tween 80 | 7.2 |
| Talc T1005 | 11.5 |
| Ethanol 190P | 21.3 |
| | 100.0 |
| | % solids (theoretical) 35% |

The foregoing pre-mix solution has a viscosity of from about 2000 to 2800 cps, and a theoretical percent solids of about 35%.

This premix is then added to the active ingredient solution which comprises PVP-I dissolved in Ethanol 190P (30% solids) and N-9 dissolved in Ethanol 190P (30% solids) which have been combined to form the active ingredient solution. The PVP-I solution has a viscosity of about 75 cps and the N-9 solution has a viscosity of about 4.2 cps. The combined solution, at 30% solids, and a ratio of 93.3% PVP-I to 6.7% N-9 has a viscosity of about 60 to 70 cps.

| Active ingredient Solution (1C) | |
| --- | --- |
| Component | Percent |
| PVP-I Solution (30%) | 93.3 |
| N-9 Solution (30%) | 6.7 |
| | 100.0 |
| | % solids (theoretical) = 30% |

The finished coating composition exhibits 31.4% solids (theoretical) and a viscosity in the range of 90 to 130 cps.

| FORMULATION I Preferred Coating Formulation | |
| --- | --- |
| Component | Percent |
| Active Ingredient Solution (IC) | 71.5 |
| Premix (1B) | 28.5 |
| | 100.0 |
| | % solids (theoretical) = 31.4% |

As will become apparent to the skilled artisan, there are many variations to the foregoing, falling within the recited component ranges, which are equally well suited for use as described herein. For instance, a formulation having a lower % solids would be better suited to spray and dip coating techniques. The foregoing is merely one embodiment of the composition, included as a means of more fully disclosing the subject coating composition and a method of making the same. The foregoing solution is well suited for coating by the reverse roll and rod coating methods on a paper or film, or suitable laminated substrates. Generally, the coating composition, having an active ingredient concentration of 25% to 80% of the coat weight on dry basis, is coated at a coat weight of 6 to 12 oz. per 384 ft$^2$. In the foregoing, the active ingredient concentration equates to about 140 to 760 µg/cm$^2$ on a given substrate.

DESIGN ALTERNATIVES

Alternative Coating Techniques for Coating Various Substrates

As has been shown hereinabove, many paper substrates coat well by the reverse roll method using the General Coating Formulation with a percent solids about 30% to 32%. Percent solids below about 10–15% are generally not desirable with this technique due to high cost of lost solvent (volatiles) and because viscosities tend to be too low in this solids range resulting in poor coating quality and difficulty in achieving sufficient coat weight. Conversely, above the 50% solids range, problems with high viscosity and coating quality can be experienced, and it can then be difficult to achieve lower coat weights. This, of course, is a general observation, assuming a reverse roll or other traditional coating technique, and will change depending on the coating method actually used.

Some substrates, however, do not wet out to the level preferred herein with the General Coating Formulation. For example, some paper substrates, such as Jen-Coat's 19 lb. Semi-Crepe/5 lb. LDPE which is a paper/film laminated substrate in which the semi-crepe paper is laminated to low density polyethylene, do not adequately wet out, or accept the coating. Some non-woven laminates can also experience a problem. These instances represent another embodiment of the subject invention wherein the percent solids of the formulation can be lowered, which improves the wetting action of the coating on the substrate, and still permits an acceptable coating anti-pathogenic activity level. Non-woven laminates which can be successfully coated by the reverse roll method by lowering the percent solids of the formulation to a range of about 25% solids include Poly-Breathe II, made by PolyBond Incorporated, which is a breathable film composite in which spunbond polypropylene non-woven fabric is laminated to a heavy duty microporous film.

There are, however, some non-woven laminates such as a two-phase wet formed non-woven substrate, available from the Dexter Corporation as Grade 11160 Fabric (1992), and a drapable, non-woven water and alcohol repellent fabric, also available from Dexter Corporation, as Grade 3557 fabric (1993), sterilizable by ethylene oxide, steam or radiation, which are not easily reverse roll coatable using the subject formulation even at a lowered percent solids range of about 20% solids. These non-woven laminates are, however, coatable by the rod coating method and enable use of the formulation at a 30% to 32% solids range, thus eliminating solvent waste problems. This is yet another embodiment of the invention.

The following table summarizes the results of testing conducted on various substrates with varying levels of percent solids in the coating formulation and by the reverse roll and rod coating methods.

TABLE I

| | Pilot Coating Run - Formulation I at % Solids Shown | | | | |
| --- | --- | --- | --- | --- | --- |
| | Reverse Roll Coating (50 FPM) | | | | Rod Coating (50 FPM) |
| | @ % Solids of: | | | | |
| Substrate | @ 31.4% | @ 28.0% | @ 25.0% | @ 20.0% | @ 31.4% |
| Coastal 13# BL MG PR HWS (i) | OK | | | | |
| Jen-Coat Semi-Crepe Laminate (ii) | | Fair-slight White Spotting | OK | | |
| Poly-Breathe II (Poly Bond) (iii) | | | OK | | |
| Dexter # 11160 (iv) | | NG-Poor Wetting | | NG | |

TABLE I-continued

Pilot Coating Run - Formulation I at % Solids Shown

|  | Reverse Roll Coating (50 FPM) | | | | Rod Coating (50 FPM) |
| --- | --- | --- | --- | --- | --- |
|  | @ % Solids of: | | | | |
| Substate | @ 31.4% | @ 28.0% | @ 25.0% | @ 20.0% | @ 31.4% |
| Dexter # 3557 (v) |  |  | NG-Poor Wetting | NG-but improved | OK |

(i) 13# wood pulp processed with cellulosic fibers, light weight, flushable
(ii) 19# semi crepe/5# low density polyethylene laminate
(iii) spunbond polypropylene non-woven fabric/microporous film laminate
(iv) 2 phase wet formed, non-woven laminate
(v) drapable, non-woven water and alcohol repellent fabric A further alternative to solve coating pick-up problems on some substrates is to use substrates which have been treated to enhance coating acceptance. For example, certain non-woven laminates, including some polyester non-woven/low density polyethylene (LDPE) film lamination substrates, exhibit poor adhesion of the coating to the substrate. Post-treatment of the laminate by corona treatment, which is a process in which the substrate is bombarded with a high voltage electrical discharge thereby causing an increase in surface tension on the polyethylene film side of the laminate, increases the surface tension of the substrate, thus enhancing adhesion of the coating to the substrate.

The foregoing discussion and data clearly demonstrate the viability of the subject coating formulation on many substrates and for many applications by optimization of the formulation, the substrate, the coating method, or a combination thereof, the parameters being highly dependent on the particular application for which the substrate is intended.

Using the subject formulation or composition, as described hereinabove, there are a multitude of coating options available to the skilled artisan. Various types of products encompassing some of these options are exemplified herein as a means of more fully describing the parameters of the subject invention.

Anti-Bacterial/Anti-Vital Coating Formulations with Improved Water Resistance

In another embodiment of the invention, the subject coating formulation may be modified to render the coating less prone to leaching, i.e. the coating will have enhanced water resistance. The subject coating functions by acting as a barrier to pathogenic substances when dry, and becomes activated when wet to immediately eliminate the bacterial or viral effect of the pathogen. If the coating is totally water insoluble, it will not be effective in killing blood-or fluid-borne pathogens upon contact of the coating with the pathogens. Therefore, the coating must be at least partially water soluble in order to function. In some instances, however, it is desirable to reduce the degree of water solubility, thus improving water resistance and reducing the tendency of the coating to leach from the substrate upon contact with water or fluid.

One approach to increasing water resistance of the coating is to add to the formulation a material which is insoluble in water, but which would be soluble in an ethanol/water mixture, because this mixture is used as the solvent for the formulation. One such material is zein, which is a prolamine physically extracted from corn gluten. It forms films which are clear, odorless, tasteless and hard, and is suitable for human ingestion. Zein is insoluble in water and in anhydrous alcohol, but is soluble in a mixture of the two.

The degree to which the water resistance of the coating is enhanced by the addition of zein is a function of the concentration of the zein for a given substrate. For example, in a composition similar to that disclosed hereinabove, wherein the active ingredient solution is 54.8% by weight of the formulation and the pre-mix is 45.2% by weight of the formulation, zein may be added to the premix as a 17.6% component of a solution which comprises 50.0% by weight of the pre-mix solution, the remainder of the pre-mix solution comprising a carbowax solution as previously described.

FORMULATION II
Zein Water Resistant Coating Formulation

| Component | | Percent |
| --- | --- | --- |
| Active Ingredient Solution (40% solids) | | 54.8 |
| PVP-I (40% in Ethanol 190P) | 93.3% | |
| N-9 (40% Igepal CO-630 in Ethanol 190P) | 6.7% | |
| Pre-mix Solution | | 45.2 |
| Zein Solution (25% solids) | 50.0% | |
| Zein P4000 | (17.6) | |
| Talc T1005 | (4.4) | |
| Tween 80 | (3.0) | |
| Ethanol 190P | (60.0) | |
| Distilled H$_2$O | (15.0) | |
| Carbowax Solution (20% solids)* | 50.0% | |
| Carbowax 8000 | (20.0) | |
| Ethanol 190P | (48.0) | |
| Distilled H$_2$O | (32.0) | |
| | | 100.0 |
| | | % solids=32.65 |

*Solution 1A from General Formula Description

This formulation had a viscosity of 96.3 cps., well within the desired range.

The formulation was tested for water resistance by coating the formulation on 17.5# James River Flexpac paper substrate by the reverse roll method. This coated substrate and the same substrate material coated in the same manner with the coating formulation hereinabove (Formulation I), not including the zein component, were subjected to water resistance testing for a ten (10) minute period. The test parameters were as follows: The average weight of the substrate sample was first determined, as was that of the same substrate with the coating formulations, with and without zein, having been applied. The coated sample was then placed in room-temperature tap water for the specified test period, i.e., 1 minute, 5 minutes, 10 minutes, etc. After the test period had been completed, the sample was removed from the water bath and excess water allowed to drain back into the bath. The sample was dried by hanging until all draining stopped and then placed in an oven, at approximately 110° F., to remove any remaining water. The weight of the sample was again measured. The amount of coating dissolved off the substrate in a specific time in water was determined by the following calculation:

$$\% \text{ coating dissolved} = \frac{\text{(initial weight} - \text{final weight)}}{\text{(initial weight} - \text{substrate weight)}} \times 100$$

The test results, as shown below, proved the zein formulation to have enhanced water resistance. All coatings were in the coat weight range of 7 to 9 oz. per $384 \text{ft}^2$.

| Water Resistance Test Results* | |
|---|---|
| Coating Formulation | Percent Coating Dissolved After 10 Minutes |
| Trial 1 - Formulation II (with zein, at 32.65% solids and 96.3 cps viscosity) | 89.19% |
| Trial 2 - Formulation III (with zein, at 32.65% solids and 96.3 cps viscosity) | 89.80% |
| Trial 3 - Formulation I (without zein, at 31.4% solids and 90–130 cps viscosity) | 94.87% |
| Trial 4 - Formulation I (without zein, at 31.4% solids and 90–130 cps viscosity) | 95.34% |

*substrate = 17.5# James River Flexpac.

A second approach available to enhance the water resistance of the formulation is to substitute an alcohol-soluble resin, or water insoluble resin, for the HPMC resin component of the premix.

| FORMULATION III | | |
|---|---|---|
| Alcohol-Soluble Resin Water Resistant Coating Formulation | | |
| Component | | Percent |
| Active Ingredient Solution (30% solids)* | | 71.5 |
| PVP-I (30% in Ethanol 190P) | 93.3% | |
| N-9 (30% in Ethanol 190P) | 6.7% | |
| Resin Solution | | 28.5 |
| 30% Butvar B98 in Ethanol 190P** | | |
| | | 100.0 |
| | | % solids = 30% |

*Solution IC from General Formulation Description.
**Polyvinyl Butyryl resin, Monsanto.

Other resins similar to the Butvar B98 may also be used, such as polyamide resins or cellulose-type resins. This represents yet another embodiment of the invention.

This formulation was tested for water resistance in the same manner as set forth with respect to Formulation II, i.e. it was coated on the same substrate material in the same manner and at the same coat weight, and tested in the same manner. These test results show even further improvement over the zein results as compared to the formulation without the alcohol-soluble resin.

| Water Resistance Test Results | |
|---|---|
| Coating | Percent Coating Dissolved After 10 Minutes |
| Butvar B98 (III) | 76.4% |

It is also possible to improve water resistance by choice of substrate. For example, Formulation I, described above, was coated on two different substrates and then tested by the method given above for water resistance. The test results were as follows:

| Water Resistance Test Results | | |
|---|---|---|
| | Percent Coating Dissolved | |
| Substrate | 1 Minute | 10 Minutes |
| James River 17.5# Flexpac[1] | 81.00% | 94.64% |
| Kimberly Clark S-60857[2] | 33.09% | 65.62% |

[1]James River 17.5# Flexpac is a wood pulp processed with cellulosic fibers.
[2]Kimberly Clark S-60857 is a cellulosic substrate with an acrylic coating.

The foregoing test results regarding water resistance of the coating prove that a number of methods have been identified by which this coating property can be manipulated to achieve water resistance for a given application while yet maintaining acceptable anti-bacterial/anti-vital activity.

Addition of Dyes or Pigments

In still another embodiment of the invention, it is possible to add or incorporate dyes and/or pigments into the subject coating formulation. The active ingredients of the subject formulation tend to give the formulation a yellow hue. While this is perfectly acceptable in some cases, for instance on many paper substrates, some non-woven substrates which begin with a blue or green color take on aesthetically unacceptable coloration once coated. Further, many users will desire certain products to exhibit specific colors, whether as an identifier of the producer or manufacturer, or merely as a matter of aesthetics.

When using a dye to aid in coloration of the coated substrate, it is preferred to add the dye to the pre-mix solution and leave the active ingredient solution undisturbed, thus maintaining the desired concentration of active ingredients. For example, the following coating formulation includes Hilton Davis FD&C Blue #1, a commercially available dye, in the pre-mix solution. Where possible, in light of desired color, solubility constraints, dispersability constraints, etc., it is preferable to use colorants, or dyes and pigments, which have been previously approved by the Federal Drug Administration (FDA) for inclusion in foods, drugs, and cosmetics. Unfortunately, there is no list of colorants which are pre-approved by the FDA for inclusion in medical/hygiene products of the type contemplated herein. Colorants pre-approved for use in foods, drugs and cosmetics are good candidates for use herein, however, given the likelihood that the toxicological criticality of foods, drugs and cosmetics is probably greater than that of the products anticipated herein, which are not intended in most cases for ingestion or assimilation into the human body, but are anticipated rather to merely have limited contact with human skin.

| FORMULATION IV | | |
|---|---|---|
| Dye-Containing Coating Formulation | | |
| Component | | Percent |
| Active Ingredient Solution* | | 72.0 |
| PVP-I (30% in Ethanol 190P) | 93.3% | |
| N-9 (30% Igepal CO 630 in Ethanol 190P) | 6.7% | |
| Premix Solution (50% solids) | | 28.0 |
| Carbowax Solution | 42.0% | |
| HPMC | 4.2% | |
| Tween 80 | 5.5% | |
| Talc T1005 | 8.8% | |
| Ethanol 190P | 16.4% | |
| Hilton Davis FD&C Blue #1 | 23.1% | |
| | | 100.00 |
| | | % solids = 35.6% |

*Solution 1C from General Formulation description.

This coating formulation exhibits a bluish-green color, much like kelly green.

In an alternative embodiment, titanium dioxide (TiO$_2$) may be substituted for the talc component of the pre-mix solution prior to addition of dyes and/or pigments. This technique is particularly useful when attempting to achieve certain colors, such as indigo blue, aqua blue, or blue-green type color. The substitution of TiO$_2$ for the talc component results in a premix solution that is very close to white. The desired dye is then added to the premix solution, taking into account the inherently yellow hue of the active ingredient solution, to achieve the desired color in the final formulation. For example, the following pre-mix solution may be used in Formulation IV, Dye-Containing Coating Formulation, in place of the recited Pre-mix Solution to achieve an indigo blue colored formulation:

| FORMULATION V | | |
|---|---|---|
| Dye-Containing Coating Formulation | | |
| Component | | Percent |
| Active Ingredient Solution* | | 72.0 |
| PVP-I (30% in Ethanol 190P) | 93.3% | |
| N-9 (30% Igepal CO 630 in Ethanol 190P) | 6.7% | |
| Pre-mix Solution (50% solids) | | 28.0 |
| Carbowax 8000 Solution | 42.00% | |
| HPMC | 4.20% | |
| Tween 80 | 5.50% | |
| TiO$_2$ | 8.80% | |
| BASF Basonyl Blue 636 | 11.55% | |
| BASF Basonyl Red NB540 | 11.55% | |
| Ethanol 190 P | 16.40% | |
| | | 100.00 |
| | | % solids = 35.6% |

*Solution 1C from General Formulation description.

Another embodiment relates to a means of achieving a desired color in the coating formulation is to disperse a pigment or pigments directly into the pre-mix solution in place of the talc component without the use of TiO$_2$. The pigment concentration can be adjusted to achieve control over the color strength.

| FORMULATION VI | | |
|---|---|---|
| Dye-Containing Coating Formulation | | |
| Component | | Percent |
| Active Ingredient Solution* | | 72.0 |
| PVP-I (30% in Ethanol 190P) | 93.3% | |
| N-9 (30% Igepal CO 630 in Ethanol 190P) | 6.7% | |
| Pre-mix Solution (44% solids) | | 28.0 |
| Carbowax 8000 Solution | 54.6% | |
| HPMC | 5.4% | |
| Tween 80 | 7.2% | |
| Sunfast Blue 15:1 (Sun Chemical) | 8.8% | |
| Ethanol 190P | 11.5% | |
| | | 100.00 |
| | | % solids = 33.9% |

*Solution 1C from General Formulation description.

Micro-Encapsulation

In yet another embodiment of the subject invention, the coating includes the use of a micro-encapsulant. In some instances, it may be desirable to produce a coated substrate which exhibits a controlled release of the anti-bacterial/anti-vital agents. Also, certain environmental or use conditions may require enhanced stability of the coating. In those applications where these concerns are prevalent, the coating may include a micro-encapsulation factor to aid in achieving the desired results.

Micro-encapsulation involves coating or sheathing a core material. Encapsulation has been used extensively in the pharmaceutical industry, and has been accomplished by both chemical and mechanical processes. Some chemical processes include complex coacervation; polymer/polymer incompatibility; in-situ polymerization, etc. Mechanical processes include spray drying and fluidized bed techniques, among others.

In the subject application, the core material would be the active ingredient combination or agent, and the encapsulation may be by polymer or wax-type outer layer. For example, one may use a polymer/polymer incompatibility technique wherein the active ingredient polymer (PVP) is water soluble and the coating polymer is not water soluble. The resulting micro-encapsulated coating exhibits enhanced stability in humid conditions and controlled release of the active ingredient upon exposure of the coating to wet conditions.

One formulation which has proven suitable for use in microencapsulation is Formulation III, which has 30% solids and uses a polymer of polyvinyl butyryl, available commercially from Monsanto under the tradename Butvar B98. As might be expected, due to the water resistant characteristic of the polymer microencapsulant, this formulation enhances the water resistance of the formulation as reported hereinabove.

| FORMULATION III | | |
|---|---|---|
| Butvar B98 Microencapsulation Coating Formulation | | |
| Component | | Percent |
| Active Ingredient Solution (30% solids)* | | 71.5 |
| PVP-I (30% in Ethanol 190P) | 93.3% | |
| N-9 (30% in Ethanol 190P) | 6.7% | |

-continued

FORMULATION III
Butvar B98 Microencapsulation Coating Formulation

| Component | Percent |
|---|---|
| Resin Solution | 28.5 |
| 30% Butvar B98 in Ethanol 190P** | |
| | 100.0 |
| | % solids = 30% |

*Solution 1C from General Formulation description.
**Polyvinyl Butyryl resin, Monsanto.

While this formulation includes a polyvinyl butyryl resin, other suitable microencapsulation resins are commercially available. Other resins may include polyamide and cellulose-type resins, among others, which exhibit a time controlled dissolution, thus ensuring continued release of the agent over extended periods of time for extended user protection.

Incorporation of the Formulation into Non-Woven Laminates

In still another embodiment of the current invention, the formulation or derivatives of the formulation can be incorporated directly into the laminate during the lamination process as opposed to the use of the formulation as only a surface coating composition. Several techniques may be used to achieve this end result, including spraying the formulation into the fibers during the lamination process, blowing the formulation into the fibers during the lamination process, and spraying or applying the formulation onto the fibers during the process.

For example, the formulation may be used in conjunction with melt blown technology/processing to produce a web having the formulation embedded therein. Specifically, in one embodiment of this aspect of the invention the formulation, diluted to an appropriate percent solids of 25%, was air blown into the fibrous stream, thus being incorporated into the web as it is being formed in a more or less three-dimensional manner.

Also, the formulation may be coated on a monolithic film, which is a thin breathable film laminated to a non-woven fabric or substrate, as discussed hereinabove. Alternatively, the film substrate portion of the laminate can first be coated with the anti-bacterial/anti-vital formulation. After coating, the film can be laminated to the non-woven substrate, thus creating a more-or-less sandwich-type arrangement.

Spray and Dip Coatings with Anti-Bacterial/Anti-Viral Properties

In yet another embodiment of the subject invention, the coating formulation is spray or dip coated on specific preformed articles, as opposed to sheeting or fabric. These coating methods, while they are suitable for the substrates thus far discussed in a limited sense depending on porosity, are readily applicable to the coating of articles or objects. By articles is meant items intended for use in medical applications, such as catheters and surgical gloves.

When using these coating methods, and depending upon the article to be coated, the active ingredient solution described above may be used directly on the article without the addition of the premix solution. Alternatively, the active ingredient solution may be diluted with ethanol to a percent solids of about 12% to 20%, which aids in capability to use the spray coating method, as well as dip coating. Of course, the full formulation as recited previously herein may be used if desired and exhibits good results at 10–20% dilution. These coating techniques may be necessary with certain non-woven substrates, as stated above, due to problems with absorbency and coating penetration.

The following shows the results of using a spray coating with and without the premix solution in terms of $I_2$ concentration levels found to be effective for the purpose set forth herein. In both instances, the formulation tested was coated onto a non-woven fabric, Precision S019/08833. Sample A below was coated with Formulation I diluted to 10% solids, and Sample B was coated with only the Active Ingredient component of Formulation I diluted to 10% solids without any premix.

| Sample | Coat Weight | $I_2$ Concentration |
|---|---|---|
| Sample A | 7–8 oz. per 384 ft$^2$ | 41.34 µg/cm$^2$ |
| Sample B | 5–6 oz. per 384 ft$^2$ | 45.88 µg/cm$^2$ |

Sample B required the use of a lower coat weight in order to achieve an equivalent $I_2$ concentration given that no premix was used and the Active Ingredient concentration is therefore higher.

Use of Formulation as Disinfectant Spray

One more embodiment of the subject invention involves the use of the subject active ingredient solution formulation in a diluted condition as a disinfecting spray, directly on surfaces which may be easily contaminated. Such surfaces include table and counter tops where fluid and tissue samples are stored or analyzed, and containers for sample storage, such as holding trays, cool storage containers, carrying cases, etc. Further, there is a need for such a spray for personal hygienic use, such as in public restroom facilities. Dilution of the solution to a 5% to 10% solids range ensures ease of use while yet maintaining the required level of anti-viral/anti-bacterial activity. Such a spray would not be toxic to human tissue which may come in contact with the spray during or immediately after use.

Evaluation of Coating Formulation

The following samples, coating and substrates as specified in TABLE II, at the stated percent solids, $I_2$ concentration and coat weight were evaluated for HIV-inactivating properties. Using the test protocol set forth in "Evaluation of Antiviral Drugs and Neutralizing Antibodies to Human Immunodeficiency Virus By a Rapid and Sensitive Microfilter Infection Assay", J. Clin. Microbiology, 1988, Vol. 26:231–235, incorporated herein by reference, virus suspensions were placed on various samples and remained on the samples for 1–2 minutes, after which a small amount of suspension was cultured for detection of infectious virus. The cultures were maintained for twelve (12) days, which is sufficient to detect as little as one (1) infectious virus particle.

The cells were observed periodically over the twelve day incubation period, and as seen under light microscopy, the results were recorded as "+" (any number of syncytia present) or "–" (no syncytia present). Cultures that remain free of syncytia after twelve days indicate that the inoculum contained no infectious virus. Further test to confirm the absence of infection involved use of the immunoassay used to detect the HIV p24 antigen.

The results of these tests showed the HIV was completely inactivated upon contact with each coated sample (Examples 1–8), but was not inactivated by contact with control samples (Examples 9–12). In these tests, virus that came in contact with control samples was detected very early by the presence of syncytia after five (5) days. In contrast, a virus inoculum that came in contact with coated samples remained free of syncytia for twelve days and had no detectable HIV p24 antigert.

TABLE II

HIV-Inactivating Properties

| Example | Coating/ Substrate | % Solids | Coating Method | Coat weight (oz./384 ft² ± 0.5 oz) | I₂ concentration (μg/cm²) | Syncytia[7] on days: 3 | 5 | 6 | 8 | 10 | 12 | p24 day 12 |
|---|---|---|---|---|---|---|---|---|---|---|---|---|
| 1 | Formulation I/ [1]James River Flexpac 17.5# | 31.4 | Reverse roll (pilot coater) | 8.1 | 41.50 | — | — | — | — | — | — | — |
| 2 | Formulation I/ [2]13# Coastal Paper BLMG HWS PR | 30.0 | Reverse roll (pilot coater) | 8.3 | 46.27 | — | — | — | — | — | — | — |
| 3 | Formulation I/ [3]K-C S-60857 | 31.4 | Rod coated (lab) | 8.3 | 41.00 | — | — | — | — | — | — | — |
| 4 | Formulation I/ [4]Poly-Breathe II | 25 | Reverse roll (pilot coater) | 8.8 | 52.04 | — | — | — | — | — | — | — |
| 5 | Formulation IV/ [1]James River Flexpac 17.5# | 35.6 | Rod coated (lab) | 8.0 | 47.52 | — | — | — | — | — | — | — |
| 6 | Formulation II/ [1]James River Flexpac 17.5# | 32.65 | Rod coated (lab) | 8.2 | 47.21 | — | — | — | — | — | — | — |
| 7 | Formulation III/ [1]James River Flexpac 17.5# | 30.0 | Rod coated (lab) | 7.8 | 46.42 | — | — | — | — | — | — | — |
| 8 | Formulated I/ [2]13# Coastal Paper BLMg HWS PR | 31.4 | Reverse roll (pilot coater) with increased oven temperature (140° F. in all zones) | 7.5 | 39.71 | — | — | — | — | — | — | — |
| 9 | No coating/ [1]James River Flexpac 17.5# | — | Uncoated | N/A | 0.00 | — | + | + | d[5] | d | d | na[6] |
| 10 | No coating/ [2]13# Coastal Paper | — | Uncoated | N/A | 0.00 | — | + | + | d | d | d | na |
| 11 | No coating/ KC S-60857 | — | Uncoated | N/A | 0.00 | — | + | + | d | d | d | na |
| 12 | No coating/ [4]Poly-Breathe II | — | Uncoated | N/A | 0.00 | — | + | + | d | d | d | na |

[1]Examining table roll paper
[2]Tissue paper
[3]Medical packaging paper
[4]Medical/surgical material
[5]Complete cell death due to infection
[6]Not applicable, due to complete virus-induced cell death
[7]Multinucleated giant cells.

A further study was conducted to determine the self sanitizing activity of an antimicrobial coated paper according to the subject invention. The test system used has been used historically for this type of study and will allow the data to be compared to that of other compounds. The study was conducted according to the protocol entitled, "Evaluation of Self Sanitizing Activity of an Antimicrobial Coated Paper." The test organism was Staphylococcus aureus ATCC 6538.

Two jars were prepared, each containing ten 1⅝"×1⅝" square swatches of the control article, Example 21, and two jars were prepared, each containing ten 1⅝"×1⅝" square swatches of the test article, Example 22. One jar of each set was labeled "30 seconds" and the other "120 seconds".

Cultures S. aureus ATCC 6538 were added to the swatches in each bottle. The Samples were neutralized after desired exposure, 30 seconds or 120 seconds in 100 ml of phosphate buffer neutralizer fluid.

The samples were plated and all plates were incubated at 37°±1° C. for 48 hours prior to counting. The results are presented in Table III below.

The material identified as Example 22, Formulation I, on tissue paper (toilet seat cover tissue), an orange translucent paper, achieved a 99.9% reduction in a 30 second exposure and a >99.999% reduction after a 120 second exposure compared to the number of S. aureus recovered from the untreated control swatches, Example 21, immediate (30 second) contact time. The percent reduction of bacteria by antimicrobial treated substrate was calculated as follows:

$$\text{Percent Reduction} = \frac{B - A}{100} \times 100$$

A=The number of bacteria recovered from the treated substrate, Example 22 in the jar incubated over the desired contact period.

B=The number of bacteria recovered from the untreated control substrate Example 21, in the jar immediately after inoculation (30 seconds).

TABLE III

Sell Sanitizing Activity of Antimicrobial Coated Paper

| Example | Exposure time (seconds) | $10^0$ | $10^{-1}$ | $10^{-2}$ | $10^{-4}$ | $10^{-5}$ | $10^{-6}$ | Average CFU/ml neutralizer | No. org/tissue sample* |
|---|---|---|---|---|---|---|---|---|---|
| 21 | 30 | | | | 27 | 0 | 1 | $3.3 \times 10^5$ | $3.3 \times 10^7$ |
| 21 | 120 | | | | 39 | 10 | 0 | | |
| | | | | | 32 | 4 | 1 | $3.4 \times 10^5$ | $3.4 \times 10^7$ |
| | | | | | 35 | 4 | 0 | | |
| 22 | 30 | 270 | 28 | 2 | | | | $3.2 \times 10^2$ | $3.2 \times 10^4$ |
| | | 276 | 36 | 4 | | | | | |
| 22 | 120 | 2 | 0 | 0 | | | | $1.0 \times 10^0$ | $1.0 \times 10^2$ |
| | | 0 | 0 | 0 | | | | | |

*Number of organism/tissue sample = Number per ml neutralizer × 100 ml neutralizer

| | Inoculum Counts | | | CFU/ml |
|---|---|---|---|---|
| Test Organism | $10^{-6}$ | $10^{-7}$ | $10^{-8}$ | $3.0 \times 10^9$ |
| *Staphylococcus aureus* ATCC 6539 | TNC* | TNC | 33 | |
| | TNC | TNC | 27 | |

*Too numerous to count.

---

The subject invention has been described with reference to specific substrates, coating formulations, testing and test results, and processing techniques, all of which are included to better enable the skilled artisan to duplicate the subject invention in all its many forms. It is not intended that the invention be limited by these examples, but rather that it be accorded the full breadth of the teachings herein, including all variations and permutations thereof which are obvious to the skilled artisan given the content of this disclosure and which fall within the scope of the appended claims.

What is claimed is:

1. A method of imparting anti-pathogenic properties to a substrate material wherein said method includes preparation of an anti-pathogenic coating solution and subsequently using said coating solution to coat said substrate, said method comprising:

(a) preparing a coating composition containing an anti-pathogenic agent consisting essentially of PVP-I and N-9 in a ratio of from about 100:0 to about ):100 of PVP-I to N-9, the coating composition further containing a premix solution with which the anti-pathogenic agent is intimately mixed in a ratio of from about 6:4 to about 8:2 of agent to pre-mix on a dry basis, and having a percent solids content of from about 5% to about 35% solids, said coating composition being prepared by (i) preparing a solution of polyethylene glycol (PEG) in a mixture of alcohol and water; (ii) adding a surfactant comprising a polyethylene glycol sorbitan fatty acid ester compound and an alcohol/water solution to the PEG solution with stirring until homogeneously mixed; (iii) adding to the mixture of step (ii) a prepared powder mixture comprising hydroxypropyl methylcellulose and hydrous magnesium silicate and stirring to obtain a homogeneous solution of the power mixture of step (ii); (iv) stirring the solution of step (iii) for a time sufficient to affect a homogeneous mixture thereof; and (v) adding with stirring to the homogeneous solution of step (iv) a pre-prepared solution comprising a mixture of (1) a solution of PVP-I in an ethanol/water solvent and (2) a solution of N-9 in an ethanol/water solvent, the resulting anti-pathogenic composition exhibiting a viscosity of about 50–600 cps;

(b) feeding the anti-pathogenic coating composition into a coating machine;

(c) loading a substrate onto the coating machine;

(d) operating the coating machine such that the coating composition comes into intimate contact with at least one surface of the substrate; and (e) drying the coated substrate material.

2. The method of claim 1 wherein the coating machine is a reverse roll coating machine.

3. The method of claim 1 wherein the substrate is a paper substrate of between about 10 lb./3000 ft$^2$ and about 30 lb./3000 ft$^2$, and the coating composition used has a percent solids content of between about 20% and about 35%.

4. The method of claim 2 wherein the substrate is a laminate material and the coating composition used has a percent solids content of about 20%.

5. The method of claim 4 wherein the substrate is a paper laminated to a polymeric film.

6. The method of claim 2 wherein the substrate is a non-woven material.

7. The method of claim 1 wherein the coating machine is a rod coating machine.

8. The method of claim 7 wherein the substrate is a laminate material and the coating composition used has a percent solids content of between about 30% and about 33%.

9. The method of claim 7 wherein the substrate is a non-woven material.

10. The method of claim 1 wherein the coating machine is a spray coater and coating composition, which has a percent solids content of between about 5% and about 20%, is atomized prior to contacting the substrate.

11. The method of claim 10 wherein the substrate is selected from the group consisting of paper, non-woven material, coated paper and laminates of paper, non-woven material and polymeric film.

12. The method of claim 1 wherein the coating machine is a dip coating machine and the coating composition used has a percent solids of between about 5% and about 20%.

13. A process for producing a substrate coated with a formulation containing an anti-pathogenic component comprising:

(a) depositing onto at least one surface of a substrate material a coating formulation in solution, characterized by the inclusion of PVP-I and N-9 as the active anti-pathogenic agent in a ratio of from about 100:0 to about 0:100 respectively and further including a premix solution in a ratio of about 6:4 to about 8:2 agent:premix;

(b) fixing said coating on said substrate; and (c) drying said coated substrate such that the coated substrate, when dry, protects against air- or solution-borne pathogens and, when wet, releases the anti-pathogenic agent to substantially immediately eliminate the pathogens.

14. A coated substrate comprising a substrate material in intimate contact with an anti-pathogenic agent-containing solution characterized by the ability to release an anti-pathogenic agent immediately upon contact with a solution-borne pathogen to eliminate substantially immediately the pathogenic activity of the pathogen, wherein the anti-pathogenic agent-containing solution comprises (a) from about 30% by weight to about 80% by weight of an anti-pathogenic agent comprising a solution containing PVP-I and N-9; and (b) from about 20% by weight to about 70% by weight of a premix solution and wherein the anti-pathogenic agent-containing solution exhibits a percent solids of between about 10% and about 50% and a viscosity of between about 50 cps and about 600 cps.

15. The coated substrate as in claim 14 wherein the premix solution contains a hydrophilic polymeric binder, a nonionic suffactant, an excipient, and a solvent.

16. The coated substrate as in claim 14 wherein the premix solution contains polyethylene glycol, hydroxypropyl methylcellulose, polyoxyethylene sorbitan, hydrous magnesium silicate, and ethanol.

17. The coated substrate as in claim 14 wherein the coating solution exhibits a percent solids of from about 25% to about 35% and a viscosity of between 90 cps and 130 cps.

18. The coated substrate as in claim 14 wherein the coating solution exhibits a percent solids of about 30% to about 32% and the substrate is a paper substrate coated by the reverse roll coating method.

19. The coated substrate as in claim 14 wherein the coating solution exhibits a percent solids of about 20% and the substrate is selected form the group consisting of non-woven laminates and paper/film laminates coated by the reverse roll coating method.

20. The coated substrate as in claim 14 wherein the coating solution exhibits a percent solids of about 30% to about 33% and the substrate is a non-woven laminate coated by a rod coating method.

21. The coated substrate as in claim 14 wherein the coating composition further includes a component to enhance water resistance of the substrate.

22. The coated substrate as in claim 14 wherein the coating solution further includes a coloring component.

23. An anti-pathogenic solution comprising a solution characterized by a % solids of 31.4% and the inclusion of a solution of PVP-I and N-9 as the active anti-pathogenic agent, the components of the solution being present in a ratio of from about 100:0 to about 0:100 PVP-I:N-9 and further including premix solution, wherein on a wet weight basis the anti-pathogenic agent solution comprises 71.5% by weight active anti-pathogenic agent and 28.5% by weight premix solution, and further wherein the active anti-pathogenic agent comprises 93.3% by weight PVP-I and 6.7% by weight N-9 and the premix solution comprises 54.6% by weight polyethylene glycol solution in distilled water and ethanol, 5.4% by weight polyoxyethylene sorbitan monoolete, 11.5% by weight talc, and 21.3% by weight ethanol solvent or the equivalent dry weight for each component consistent with the recited % solids, the anti-pathogenic solution exhibiting a viscosity between about 90 cps and about 130 cps, the solution substantially completely eliminating pathogens from a surface upon contact.

24. A process for preparing an anti-pathogenic coating composition for coating paper, plastic, woven and non-woven substrates and combinations thereof, comprising:

(a) preparing a solution of polyethylene glycol (PEG) in a mixture of alcohol and water;

(b) adding a suffactant comprising a polyethylene glycol sorbitan fatty acid ester compound and an alcohol/water solution to the PEG solution with stirring until homogeneously mixed;

(c) adding to the mixture of step (b) a pre-prepared powder mixture comprising hydroxypropyl methylcellulose and hydrous magnesium silicate and stirring to obtain a homogenous solution of the powder mixture of step (b);

(d) stirring the solution of step (c) for a time sufficient to affect a homogenous mixture thereof; and (e) adding with stirring to the homogenous solution of step (d) a pre-prepared solution comprising a mixture of (1) a solution of PVP-I in an ethanol/water solvent and (2) a solution of N-9 in an ethanol/water solvent, the resulting anti-pathogenic composition having percent solids of about 25% to about 35% and a viscosity of about 50–600 cps.

* * * * *